United States Patent [19]
Feldmann et al.

[11] Patent Number: 5,647,853
[45] Date of Patent: Jul. 15, 1997

[54] RAPID RESPONSE OCCLUSION DETECTOR FOR A MEDICATION INFUSION PUMP

[75] Inventors: William G. Feldmann, Los Angeles; Vernon J. Scherbenske, Torrance; Craig M. Henning, Alhambra, all of Calif.

[73] Assignee: MiniMed Inc., Sylmar, Calif.

[21] Appl. No.: 397,797

[22] Filed: Mar. 3, 1995

[51] Int. Cl.$^6$ ............................................. A61M 1/00
[52] U.S. Cl. ........................... 604/155; 604/154; 604/31
[58] Field of Search .................................. 604/131, 151, 604/152, 154, 155, 207, 211, 246

[56] References Cited

U.S. PATENT DOCUMENTS

| | | | |
|---|---|---|---|
| 3,858,581 | 1/1975 | Kamen | 604/155 |
| 4,424,720 | 1/1984 | Bucchineri | 604/155 X |
| 4,435,173 | 3/1984 | Siposs et al. | 604/155 |
| 4,560,979 | 12/1985 | Rosskopf | 604/154 X |
| 4,562,751 | 1/1986 | Nason et al. | 74/111 |
| 4,678,408 | 7/1987 | Nason et al. | 417/410 |
| 4,685,903 | 8/1987 | Cable et al. | 604/154 |
| 4,952,205 | 8/1990 | Mauerer et al. | 604/154 X |
| 5,034,003 | 7/1991 | Denance | 604/131 X |
| 5,244,463 | 9/1993 | Cordner, Jr. et al. | 604/131 |
| 5,254,096 | 10/1993 | Rondelet et al. | 604/152 |

*Primary Examiner*—Sam Rimell
*Attorney, Agent, or Firm*—Kelly Bauersfeld Lowry & Kelley, LLP.

[57] ABSTRACT

An improved occlusion detector is provided in a medication infusion pump to monitor medication delivery to a patient, and to provide an early alarm in the event of medication nondelivery. The detector comprises a force sensor and related control circuit for reading and comparing the pressure applied to the medication at the time of pump operation to administer a dose to the patient, with the same pressure at a later point in time preceding the next dose. If the difference between the pressure readings is less than a predetermined value, an occlusion of the medication delivery line is indicated and an alarm is activated.

12 Claims, 2 Drawing Sheets

RAPID RESPONSE OCCLUSION DETECTOR FOR A MEDICATION INFUSION PUMP

BACKGROUND OF THE INVENTION

This invention relates generally to improvements in infusion pumps of the type used for controlled delivery of medication to a patient. More specifically, this invention relates to an improved occlusion detector for use in a medication infusion pump, to provide an early alarm of medication nondelivery due to an occlusion along the medication delivery flow path or other pump drive system failure.

Infusion pump devices and systems are relatively well-known in the medical arts, for use in delivering or dispensing a prescribed medication such as insulin to a patient. In one form, such devices comprise a relatively compact pump housing adapted to receive a syringe carrying a prescribed medication for administration to a patient through infusion tubing and an associated catheter or the like. The infusion pump includes a small stepping drive motor having an output connected via a lead screw assembly for motor-driven advancement of a syringe piston plunger to administer the medication to the patient. Programmable control means are normally provided for operating the drive motor at periodic intervals to obtain a closely controlled and accurate delivery of the medication over an extended time period. Such infusion pumps are utilized to administer insulin and other medications, with an exemplary pump construction being shown and described in U.S. Pat. Nos. 4,562,751; 4,678,408; and 4,685,903, which are incorporated by reference herein.

Infusion pumps of the general type described above have provided significant advantages and benefits with respect to accurate delivery of medication over an extended time period. The infusion pump is often designed to be extremely compact and may thus be adapted to be carried by the patient, for example, by means of a belt clip or the like. As a result, important medication can be administered with precision and in an automated manner, without significant restriction on the patient's mobility or life-style.

In the past, medication infusion pumps have included alarm systems designed to detect and indicate pump malfunction and/or nondelivery of the medication to the patient as a result of an occluded delivery line. Such alarm systems have typically used a high pressure limit switch for activating an alarm when the force applied to the syringe piston plunger reaches a predetermined upper limit indicative of an occluded medication delivery line. In U.S. Pat. No. 4,562,751, the high pressure switch is positioned at one end of a rotatable lead screw, wherein the mechanical reaction force or backlash between the syringe plunger and the pressure switch is proportional to the pressure applied to the medication as a result of attempted advancement of the syringe plunger. In actual practice, however, such high pressure limit switches have not provided the desired early warning of an occlusion, but instead have required multiple consecutive nondelivered doses before the pressure will rise to a level sufficient to activate the high pressure switch. For many patients, it may take several hours for the occurrence of several consecutive doses, whereby an occlusion may go undetected for an undesirably long period of time. This problem is especially significant when the patient is a child, and wherein each dose comprises a relatively small volume of the medication.

There exists, therefore, a significant need for further improvements in medication infusion pumps particularly with respect to improved and rapid response occlusion detection for providing an early warning of an occlusion or other pump drive system failure. The present invention fulfills this need and provides further related advantages.

SUMMARY OF THE INVENTION

In accordance with the invention, a medication infusion pump is provided with an improved occlusion detector for monitoring medication delivery to a patient, and to provide an early alarm in the event of medication nondelivery. The occlusion detector comprises a force sensor and a related control circuit for reading and comparing the pressure applied to the medication at specific points in time relative to pump operation to administer the medication, and for activating an appropriate alarm in the event that the monitored pressure readings indicate an occlusion of the medication delivery line.

In the preferred form, the medication infusion pump comprises a compact pump housing for receiving and supporting a syringe filled with a prescribed medication such as insulin for administration to a patient through infusion tubing and an associated catheter or the like. A small stepping drive motor within the pump housing is programmably operated at intervals to rotate a lead screw, resulting in precision translation of a lead screw nut coupled to the piston plunger of the medication-containing syringe. The piston plunger is thus advanced incrementally to deliver prescribed medication doses from the syringe and through the infusion tubing to the patient.

The force sensor of the occlusion detector is mounted at one end of the lead screw in a position for monitoring the drive force applied to the syringe piston plunger. That is, said drive force is coupled by mechanical reaction or backlash through the lead screw for detection and monitoring by the force sensor. The force detected by the sensor is directly proportional to the pressure applied to the medication within the syringe.

The control circuit causes the force sensor to read the pressure substantially at the time of administering a medication dose to the patient, and again at a later time preceding the next dose. The control circuit compares these two pressure readings, to determine whether the infusion tubing and/or catheter are occluded. Specifically, if the difference between the two pressure readings is less than a predetermined value, an occlusion is indicated and an alarm is activated. Conversely, if the compared difference is greater than said predetermined value, then the pressure applied to the medication within the syringe has dropped to reflect actual and proper medication delivery to the patient.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
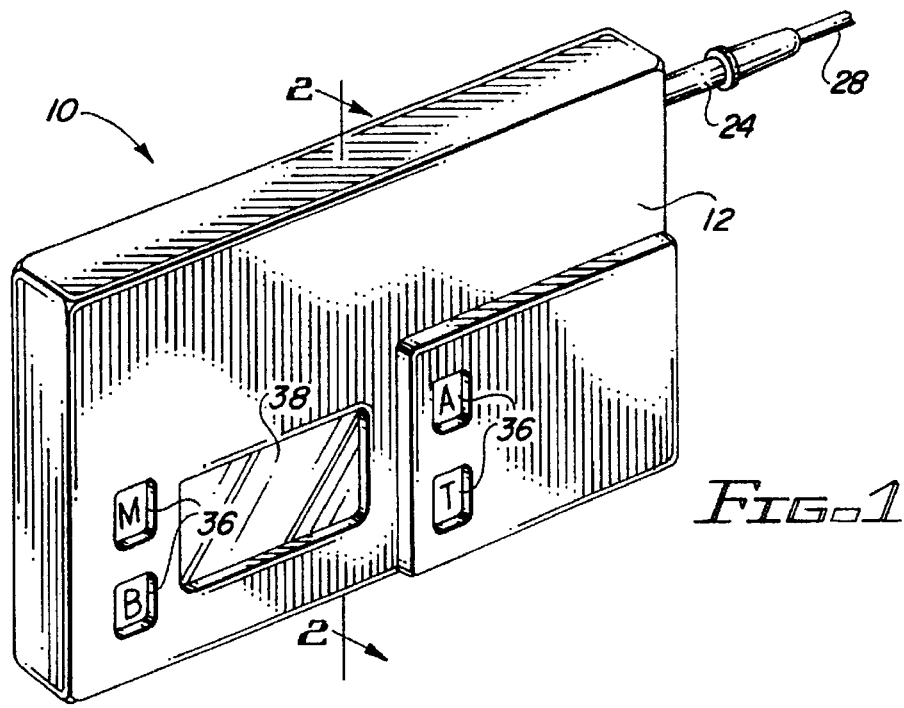
FIG. 1 is a front perspective view illustrating a medication infusion pump for controlled delivery of medication to a patient, and further adapted to include the rapid response occlusion detector embodying the novel features of the invention.

As shown in the exemplary drawings, a medication infusion pump referred to generally in FIG. 1 by the reference numeral 10 is provided for controlled administration of medication to a patient. In accordance with the invention, the infusion pump 10 includes a rapid response occlusion detector for monitoring and verifying proper delivery of the medication to the patient.

Figure 2:
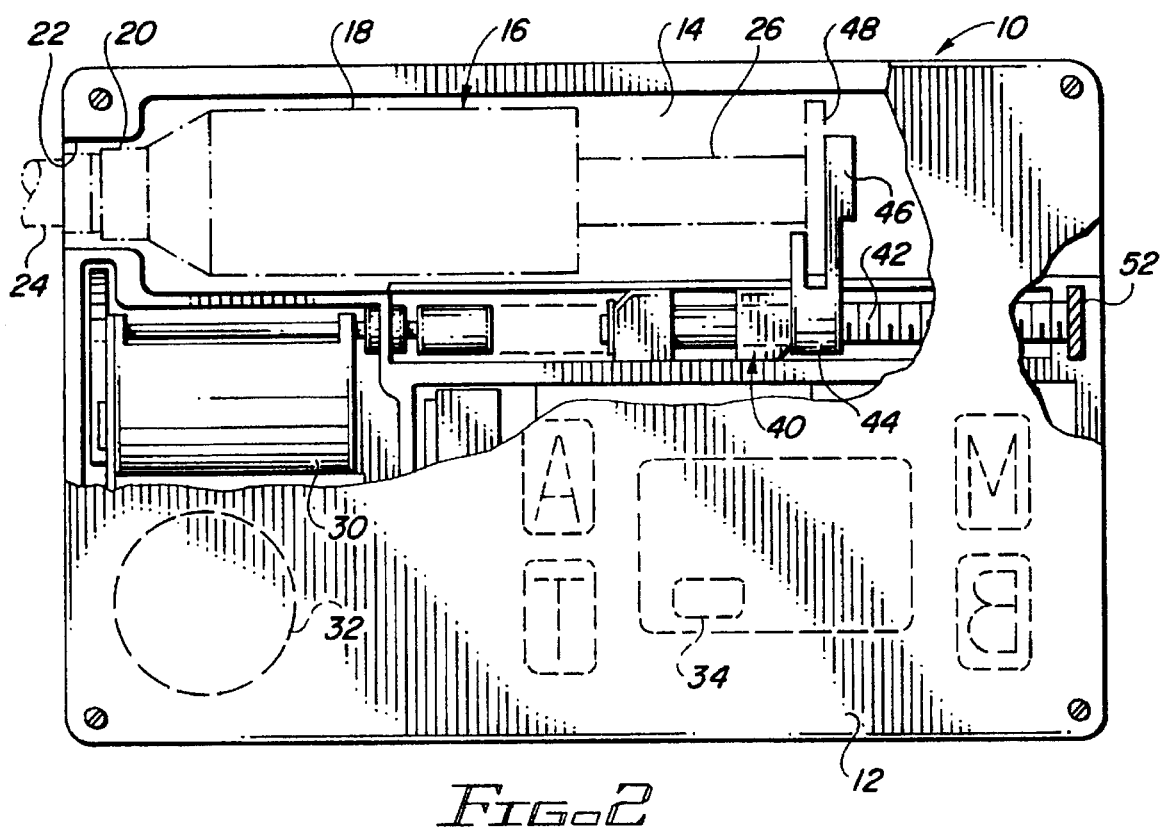
FIG. 2 is an enlarged rear elevation view of the infusion pump of FIG. 1, with portions broken away to illustrate pump operating components.

The infusion pump 10 has an overall construction and operation which is generally known in the art. More specifically, with respect to FIGS. 1 and 2, the infusion pump 10 comprises a relatively compact pump housing 12 defining an elongated chamber 14 (FIG. 2) for receiving and supporting a syringe 16 charged with a selected medication, such as insulin, to be administered to a patient. The medication-containing syringe 16 includes a syringe barrel 18 joined at the front to a luer neck 20 of reduced diametric size to seat snugly within an outlet port 22 formed in the pump housing 12. A luer fitting 24 is carried on the neck 20 and cooperates with the barrel 18 to fix the syringe in a seated position within the syringe chamber 14. A syringe piston or plunger 26 extends from the aft end of the barrel 18 and may be advanced into the barrel to deliver the medication therefrom. In this regard, the medication is normally dispensed to the patient through a catheter tube 28 or the like adapted for appropriate connection to the luer fitting 24.

The infusion pump 10 includes a compact stepping drive motor 30 (FIG. 2) which is mechanically connected to the syringe plunger 26 for purposes of advancing the plunger in a precision controlled manner to dispense the medication. In this regard, the drive motor 30 is normally powered by a battery power supply 32 or the like, in response to operation of a programmable controller 34. As known in the art, the programmable controller 34 can be set by the attending physician, appropriate medical personnel, or the user by an array of buttons 36 on the face or front of the pump housing 12, with a corresponding display panel 38 providing appropriate information regarding set status and/or pump operation. The controller 34 operates the drive motor 30 in a stepwise manner, typically on an intermittent basis, to administer discrete precision doses of the medication to the patient at programmed times.

The mechanical connection between the stepping drive motor 30 and the syringe plunger 26 includes a lead screw assembly 40. More specifically, the drive motor 30 has a rotary output for rotatably driving an elongated lead screw 42 mounted within the pump housing 12. A lead screw nut 44 is carried on the lead screw 42 and includes an appropriate latch arm 46 for engaging a drive flange 48 on the end of the piston plunger 26. Appropriate rotation of the lead screw 42 in response to operation of the stepping motor 30, causes the lead screw nut 44 and associated latch arm 46 to be translated in a precision manner to correspondingly advance the piston plunger 26 and thereby deliver the medication from the syringe barrel 18 and through the catheter tube 28 to the patient. Further details regarding the construction and operation of a medication infusion pump of this general type can be found in U.S. Patent Nos. 4,562,571; 4,678,408; and 4,685,903, which are incorporated by reference herein.

The occlusion detector of the present invention is designed to provide early warning of system malfunction, particularly nondelivery of a medication dose to the patient as a result of an occluded medication flow path. In this regard, in general terms, translation of the lead screw nut 44 and the latch arm 46 to deliver medication from the syringe 16, will be accompanied by a rise in pressure applied to the medication within the syringe barrel 18. During normal operation with proper medication delivery to the patient, that pressure rise will subside within a relatively short period of time, reflecting medication flow out of the syringe barrel 18 and through the catheter tube 28 to the patient. However, if the flow path is obstructed, the pressure rise will not subside to any substantial degree. Consecutive attempts to administer medication to the patient will result in a stepwise increase in the pressure applied to the medication within the syringe barrel.

The occlusion detector of the present invention monitors the pressure applied to the medication at spaced-apart points in time, to determine whether an occluded flow line condition exists. If the pressure reading comparison is less than a predetermined value, indicative of little or no subsiding in medication pressure following a dispense event, then an occlusion condition is promptly detected so that an appropriate alarm 50 (FIGS. 3 and 4) such as an audible alarm can be activated. Conversely, if the monitored pressure difference exceeds the predetermined value, reflective of proper subsidence in pressure level over a period of time, then normal pump medication delivery is indicated.

The occlusion detector includes a force sensor 52 such as a variable resistor force sensor of the type marketed by Interlink Electronics of Camarillo, Calif., under the product designation FSR. As shown best in FIG. 2, the force sensor 52 is mounted on the pump housing 12 at one end of the lead screw 42. The force sensor 52 is positioned to monitor an axial reaction or backlash force applied to the lead screw 42 via the piston plunger 26 and the associated lead screw nut 44, when the lead screw 42 is rotated upon attempted delivery of the medication to the patient. Accordingly, the force sensor 52 detects a force which is directly proportional to the pressure applied to the medication within the syringe barrel 18.

Figure 3:
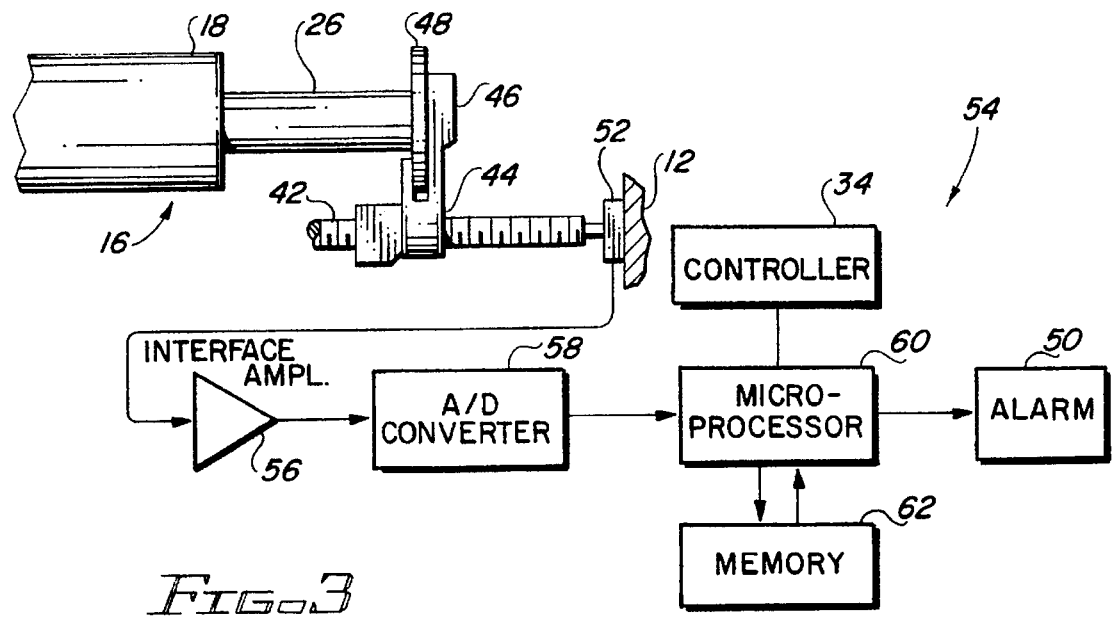
FIG. 3 is a schematic circuit diagram illustrating the occlusion detector.

As shown in FIG. 3 in one preferred form, the force sensor 52 provides an input signal to a control circuit 54 which is coupled with the pump programmable controller 34. As shown, the control circuit 54 includes an interface amplifier 56 and an analog-to-digital converter 58 for conditioning the output signal of the force sensor 52 and for supplying that output signal to a microprocessor 60 for storage and subsequent processing functions. The microprocessor 60 is operated by the controller 34 to read and store the force reading outputs from the force sensor 52 in a memory 62. These force readings are taken substantially at the time of medication administration to the patient, i.e., immediately after lead screw rotation to advance the position plunger 26, and at a later time shortly preceding the next dose. These readings are compared to provide an indication of proper medication delivery, or nondelivery, as described above.

More particularly, the pressure applied to the medication within the syringe barrel 18 is relatively high when the syringe plunger 26 is advanced during a delivery event. However, this pressure will subside relatively quickly if the medication delivery path is unobstructed, since the pressure will be relieved by delivery of the medication dose to the patient. Conversely, if the delivery path is occluded, the pressure applied to the medication will not subside to a substantial degree. Accordingly, by comparing the readings from the force sensor 52 during a delivery event and at a later time such as shortly before the next delivery event, accurate occlusion monitoring is obtained. If the compared readings exceed a predetermined level indicative of substantial subsiding of the pressure within the syringe barrel 18, then proper medication delivery is indicated. However, if the compared readings are the same or otherwise less than said predetermined level, then nondelivery attributable to an occluded flow path is indicated.

In the preferred form, to prevent false alarms, the controller 34 and microprocessor 60 can be set to require a minimum number of perhaps two to four consecutive detected occlusion events before activating the alarm 50. This number of nondelivered doses, however, can be sufficiently small in number to provide the desired early occlusion warning for juvenile patients.

In addition, the system can be programmed to provide other alarm functions, particularly such as detecting failure of the lead screw 42 to rotate in response to operation of the stepping motor 30. In this mode, the microprocessor 62 reads force signals for the force sensor 52 immediately before and after stepping motor operation. If the monitored force signals are reflective of a pressure rise within the syringe barrel 18, in response to the desired advancement of the syringe plunger 26, then normal operation is indicated. However, if no pressure rise is detected by comparing these force readings, then the syringe plunger 26 has not been advanced as a result of some drive system failure, whereupon the alarm 50 can be activated.

A further safeguard is desirably included in the control circuit 54 to prevent false alarms during initial primary of the infusion line 28. In this process, the controller 34 and microprocessor 60 are set to ignore pressure-indicative output signals from the force sensor 52 unless and until those signals exceed a predetermined low level threshold. That is, during normal operation with the tubing 28 primed, pressures below the low level threshold are not encountered.

Figure 4:
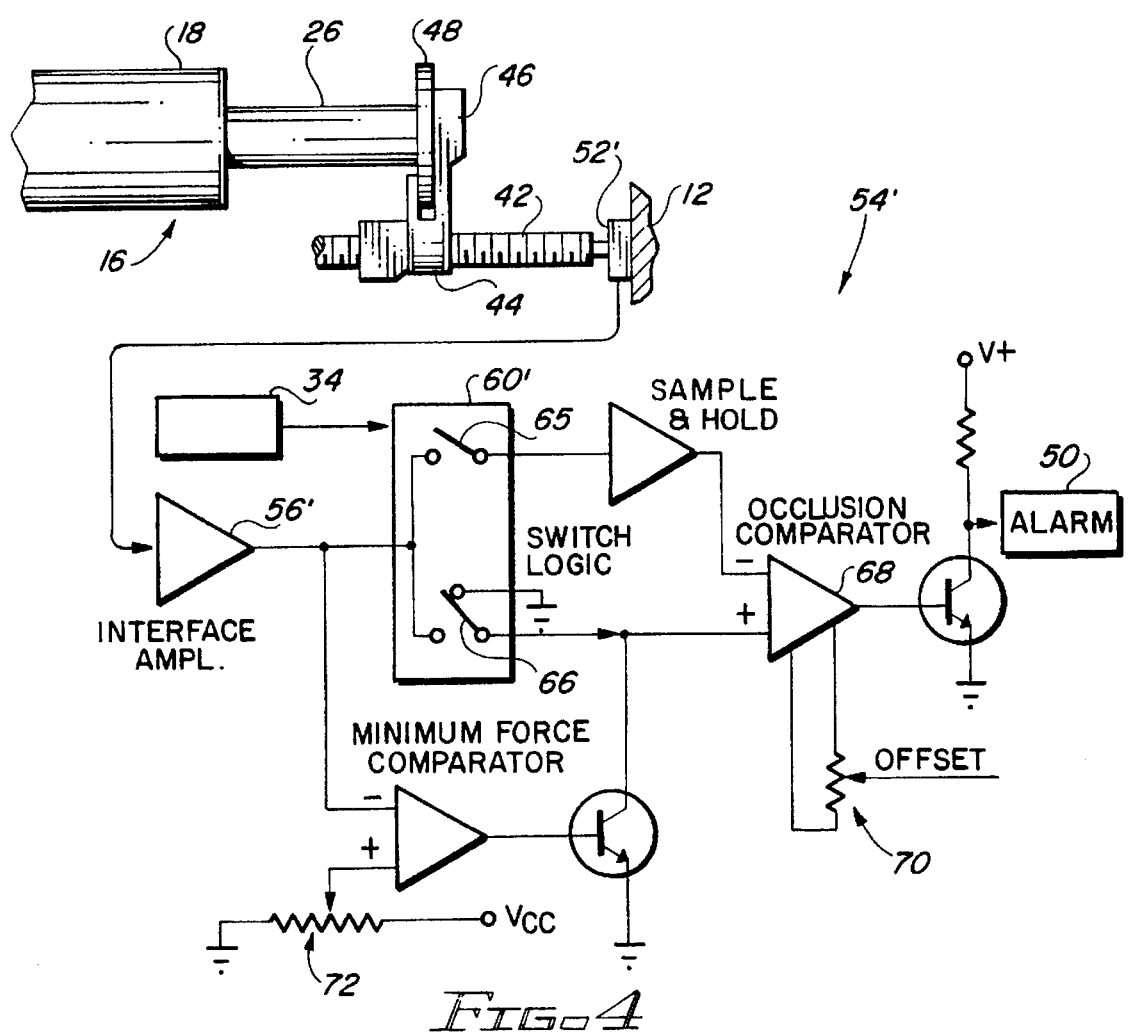
FIG. 4 is a schematic circuit diagram depicting an alternative preferred form of the invention.

FIG. 4 illustrates one alternative form of the control circuit, wherein components corresponding functionally to those shown and described in FIG. 3 are identified by common primed reference numerals. As shown, the force sensor 52' is coupled by an interface amplifier 56' to a switch logic circuit 60'. The programmable controller 34 operates the circuit 60' to read and store force readings at a time substantially corresponding with medication delivery to the patient, and at a later time shortly preceding the next dosage, by appropriate opening and closure, respectively, of a pair of switches 65 and 66 for coupling these readings to the minus and plus inputs of a comparator 68. The force readings are compared by the comparator 68, and an appropriate alarm 50 is activated when the difference between the compared readings is less than a predetermined value indicative of an occlusion, as described previously with respect to FIG. 3. A variable resistor offset 70 is inputted to the comparator 68 to set the difference threshold required to activate the alarm. In addition, a minimum force comparator circuit 72 is desirably provided to disable the comparator 68 when the detected force levels are sufficiently low to indicate a pump priming procedure.

The invention thus provides accurate and rapid response occlusion detection by monitoring pressure differentials at predetermined points in time relative to medication delivery events. With this approach, an occlusion condition or other drive system failure can be detected promptly, without requiring any significant number of consecutive delivery failures and a corresponding prolonged period of medication nondelivery to a patient. Rapid occlusion detection can be particularly important to those patients who receive medication doses of very small volumes, particularly patients such as children.

A variety of further modification and improvements to the invention will be apparent to those skilled in the art. Accordingly, no limitation on the invention is intended by way of the foregoing description and accompanying drawings, except as set forth in the appended claims.

What is claimed is:

1. A rapid response occlusion detector for use with a medication infusion pump having a syringe defining a chamber with medication therein, infusion tubing for connecting the medication chamber to a patient, a piston plunger for advancement into the medication chamber to administer a dose of the medication to the patient, and drive means for controllably advancing the piston plunger into the medication chamber to administer a succession of discrete doses of the medication to the patient, said occlusion detector comprising:

force sensor means for monitoring and for providing output signals representative of the pressure applied to the medication within the medication chamber;

control circuit means connected to said force sensor means for receiving said output signals, said control circuit means including comparator means for comparing the difference between a first output signal corresponding to a first first pressure substantially at a point in time corresponding with advancement of the syringe plunger to administer a medication dose and a second output signal corresponding to a second pressure at a later point in time substantially after said plunger advancement but preceding the next dose; and alarm means activated by said control circuit means when the difference between said first and second output signals is less than a predetermined value.

2. The rapid response occlusion detector of claim 1 wherein the drive means comprises a lead screw assembly including a lead screw rotatably supported within a pump housing, a lead screw nut threadably carried on said lead screw and including means connected to the syringe plunger, and a stepping motor for rotatably driving the lead screw, said force sensor means comprising a variable resistor force detector mounted between one end of said lead screw and the pump housing to detect a reaction force applied to the lead screw in proportion to the pressure applied to the medication within the medication chamber.

3. The rapid response occlusion detection of claim 1 wherein said control circuit means includes means for preventing activation of said alarm means until the difference between said first and second output signals is less than said predetermined value for a predetermined consecutive number of doses.

4. The rapid response occlusion detector of claim 1 wherein said control circuit means includes means for preventing activation of said alarm means unless the first output signal exceeds a predetermined low level limit.

5. The rapid response occlusion detector of claim 1 wherein said control circuit means further includes means for comparing the difference between a third output signal substantially at a point in time immediately preceding advancement of the syringe plunger to administer medication and a fourth output signal at a later point in time corresponding with advancement of the syringe plunger to administer medication, said alarm means being activated by said control circuit means when the difference between said third and fourth output signals is less than a predetermined value.

6. A method of detecting an occlusion condition in a medication infusion pump having a syringe defining a chamber with medication therein, infusion tubing for connecting the medication chamber to a patient, a piston plunger for advancement into the medication chamber to administer a dose of the medication to the patient, and drive means for controllably advancing the piston plunger into the medication chamber to administer a succession of discrete doses of the medication to the patient, said method comprising the steps of:

monitoring and providing output signals representative of the pressure applied to the medication within the medication chamber;

comparing the difference between a first output signal corresponding substantially at a point in time with advancement of the syringe plunger to administer a medication dose and a second output signal at a later point in time substantially after said plunger advancement but preceding the next dose; and activating an alarm when the difference between said first and second output signals is less than a predetermined value.

7. The method of claim 6 wherein the drive means comprises a lead screw assembly including a lead screw rotatably supported within a pump housing, a lead screw nut threadably carried on said lead screw and including means connected to the syringe plunger, and a stepping motor for rotatably driving the lead screw, said pressure monitoring step comprising detecting a reaction force applied to the lead screw in proportion to the pressure applied to the medication within the medication chamber.

8. The method of claim 6 further including the step of disabling the alarm until the difference between said first and second output signals is less than said predetermined value for a predetermined consecutive number of doses.

9. The method of claim 6 further including the step of disabling the alarm unless the first output signal exceeds a predetermined low level limit.

10. The method of claim 6 further including the steps of comparing the difference between a third output signal substantially at a point in time immediately preceding advancement of the syringe plunger to administer medication and a fourth output signal at a later point in time corresponding with advancement of the syringe plunger to administer medication, and activating the alarm when the difference between said third and fourth output signals is less than a predetermined value.

11. A failure mode detector for use with a medication infusion pump having a syringe defining a chamber with medication therein, infusion tubing for connecting the medication chamber to a patient, a piston plunger for advancement into the medication chamber to administer a dose of the medication to the patient, and drive means for controllably advancing the piston plunger into the medication chamber to administer a succession of discrete doses of the medication to the patient, said failure mode detector comprising:

force sensor means for monitoring and for providing output signals representative of the pressure applied to the medication within the medication chamber;

control circuit means connected to said force sensor means for receiving said output signals, said control circuit means including comparator means for comparing the difference between first and second output signals taken at different selected points in time wherein a failure mode is indicated when said difference is outside a predetermined range; and alarm means activated by said control circuit means when said difference indicates a failure mode.

12. A method of detecting a failure mode in a medication infusion pump having a syringe defining a chamber with medication therein, infusion tubing for connecting the medication chamber to a patient, a piston plunger for advancement into the medication chamber to administer a dose of the medication to the patient, and drive means for controllably advancing the piston plunger into the medication chamber to administer a succession of discrete doses of the medication to the patient, said method comprising the steps of:

monitoring and providing output signals representative of the pressure applied to the medication within the medication chamber;

comparing the difference between first and second output signals taken at different selected points in time wherein a failure mode is indicated when said difference is outside a predetermined range; and activating an alarm when said difference indicates a failure mode.

\* \* \* \* \*